US008452402B2

(12) United States Patent
Ecker et al.

(10) Patent No.: US 8,452,402 B2
(45) Date of Patent: May 28, 2013

(54) OPTICAL SENSING DEVICE FOR USE IN A MEDICAL DEVICE

(75) Inventors: Robert M. Ecker, Lino Lakes, MN (US); Jonathan L. Kuhn, Ham Lake, MN (US); James D. Reinke, Maple Grove, MN (US); Can Cinbis, Shoreview, MN (US); Timothy J. Davis, Coon Rapids, MN (US); Paul F. Gerrish, Phoenix, AZ (US); Jonathan P. Roberts, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1435 days.

(21) Appl. No.: 12/107,921

(22) Filed: Apr. 23, 2008

(65) Prior Publication Data

US 2009/0270953 A1 Oct. 29, 2009

(51) Int. Cl.
*A61B 5/1455* (2006.01)

(52) U.S. Cl.
USPC ............. 607/23; 600/317; 600/325; 600/333

(58) Field of Classification Search
USPC .......... 607/2; 362/267, 297, 296.04; 250/553; 600/333, 310, 317, 325
See application file for complete search history.

(56) References Cited

U.S. PATENT DOCUMENTS

| 4,202,339 | A | | 5/1980 | Wirtzfeld et al. | |
|---|---|---|---|---|---|
| 4,467,807 | A | | 8/1984 | Bornzin | |
| 4,684,991 | A | * | 8/1987 | Forchheimer et al. | 348/309 |
| 4,730,389 | A | | 3/1988 | Baudino et al. | |
| 4,815,469 | A | * | 3/1989 | Cohen et al. | 600/333 |
| 5,730,125 | A | | 3/1998 | Prutchi et al. | |
| 5,902,326 | A | * | 5/1999 | Lessar et al. | 607/36 |
| 6,134,459 | A | * | 10/2000 | Roberts et al. | 600/333 |
| 6,198,952 | B1 | * | 3/2001 | Miesel | 600/339 |
| 6,997,879 | B1 | | 2/2006 | Turcott | |
| 7,120,481 | B2 | * | 10/2006 | Keller et al. | 600/339 |
| 7,199,438 | B2 | * | 4/2007 | Appelt et al. | 257/433 |
| 8,089,079 | B2 | * | 1/2012 | Lee | 257/89 |
| 8,216,134 | B2 | * | 7/2012 | Ries et al. | 600/300 |
| 2003/0030808 | A1 | * | 2/2003 | Marshall et al. | 356/406 |
| 2003/0055324 | A1 | | 3/2003 | Wasserman | |
| 2004/0161853 | A1 | * | 8/2004 | Yang et al. | 436/164 |
| 2004/0184270 | A1 | * | 9/2004 | Halter | 362/296 |
| 2006/0149145 | A1 | * | 7/2006 | Furnary et al. | 600/325 |
| 2006/0226336 | A1 | * | 10/2006 | York et al. | 250/206 |
| 2007/0239215 | A1 | | 10/2007 | Bhumia et al. | |

FOREIGN PATENT DOCUMENTS

| WO | 2004091719 | 10/2004 |
|---|---|---|
| WO | 2009038996 | 3/2009 |

OTHER PUBLICATIONS

Mendelson, et al., "Design and Evaluation of a New Reflectance Pulse Oximeter Sensor", Medical Instrumentation, vol. 22, No. 4, Aug. 1988, pp. 167-173.

* cited by examiner

*Primary Examiner* — Christopher D Koharski
*Assistant Examiner* — Michael Carey
(74) *Attorney, Agent, or Firm* — Stephen W. Bauer; Evans M. Mburu (57) ABSTRACT

A reflectance-type optical sensor includes one or more photodiodes formed in a semiconductor substrate. A well having sidewalls and a bottom is formed in the top surface of the substrate, and a reflective layer is formed on the sidewalls and bottom. A light-emitting diode (LED) is mounted in the well, so that light emitted laterally and rearwardly from the LED strikes the sidewalls or bottom and is redirected in a direction generally perpendicular to the top surface of the substrate. The optical sensor can be fabricated using microelectromechanical systems (MEMS) fabrication techniques.

42 Claims, 6 Drawing Sheets

OPTICAL SENSING DEVICE FOR USE IN A MEDICAL DEVICE

BACKGROUND

The present disclosure relates to optical devices that include light emitting diodes (LEDs). In particular, the disclosure relates to miniaturized reflectometers which may be used, for example, in an implantable medical device (IMD).

Implantable medical devices, such as implantable pacemakers and implantable cardioversion defibrillators, monitor cardiac activity to detect various types of cardiac arrhythmias and to provide appropriate therapy based upon the type of arrhythmia detected. Cardiac arrhythmia detection is generally based upon an analysis of one or more electrical and hemodynamic functions of the heart.

ICDs are used to deliver high-energy cardioversion or defibrillation shocks to a patient's heart when atrial or ventricular fibrillation is detected. Cardioversion shocks are typically delivered in synchrony with a detected R-wave when fibrillation detection criteria are met. Defibrillation shocks are typically delivered when fibrillation criteria are met, but the R-wave cannot be discerned from signals sensed by the ICD.

Delivery of a cardioversion or defibrillation shock can be painful to the patient, and consumes energy from the battery of the ICD. It is desirable, therefore, that shocks be delivered only when they are necessary.

Sensing of additional physiologic parameters may be useful in enhancing arrhythmia detection and a determination of appropriate therapy, as well as for other physiologic monitoring and therapy applications. Among the sensors proposed for use with implantable medical detectors are optical hemodynamic sensors and tissue perfusion sensors. These optical sensors include one or more light sources (such as light-emitting diodes) and a photodetector, such as a photodiode. Multiple wavelengths of light may be emitted by the light-emitting diodes, and the amount of reflected light at each wavelength can be detected and processed to generate an output signal for use by the implantable medical device as part of its arrhythmia detection analysis, physiologic monitoring, or other therapy applications.

BRIEF SUMMARY

An optical device includes a light-emitting diode (LED) mounted at the bottom of a pyramidal well in a substrate. The well has a flat bottom surface and inclined sidewalls that slope upward and outward from the bottom surface. A reflective coating on the sidewalls of the well, the bottom of the well, or both acts as an optical mirror for light from the LED.

In one aspect, the optical device is a reflectance-type optical sensor (or reflectometer) which includes a photodetector, an optical mirror, and a light-emitting diode (LED) carried by a common substrate. The photodetector is formed in or on the substrate. The LED is mounted on the bottom surface of a pyramidal well that has inclined sidewalls and a flat bottom surface. A reflective coating within the well (e.g. on the sidewalls and bottom of the well) acts as an optical mirror to direct light from the LED in a direction that is generally perpendicular to the surface of substrate.

The optical device may be fabricated as an integrated structure using microelectromechanical systems (MEMS) fabrication techniques. The well is formed by selectively etching the substrate. The reflective layer is typically a metal layer deposited on the inclined sidewalls and bottom of the well. The LED is mounted in the well, with its top surface below the surface of the substrate, so that light emitted generally laterally or rearwardly by the LED will strike the reflective layer and then be reflected in a direction that is generally perpendicular to the surface of the substrate.

DETAILED DESCRIPTION

The present disclosure includes an optical device having an LED mounted in a well, with a reflective coating on the well to act as an optical mirror. One implementation is an optical sensor which can be used in conjunction with an implantable medical device, such as an ICD, a pacemaker, or a cardiac monitor, to detect physiologic changes correlated with modulated light signals. In the following description the optical sensor will be described in the context of an ICD, where the optical sensor produce signals that can be used in identifying cardiac arrhythmias. The optical sensor, however, can be used in a wide variety of devices for medical and non-medical applications.

Figure 1:
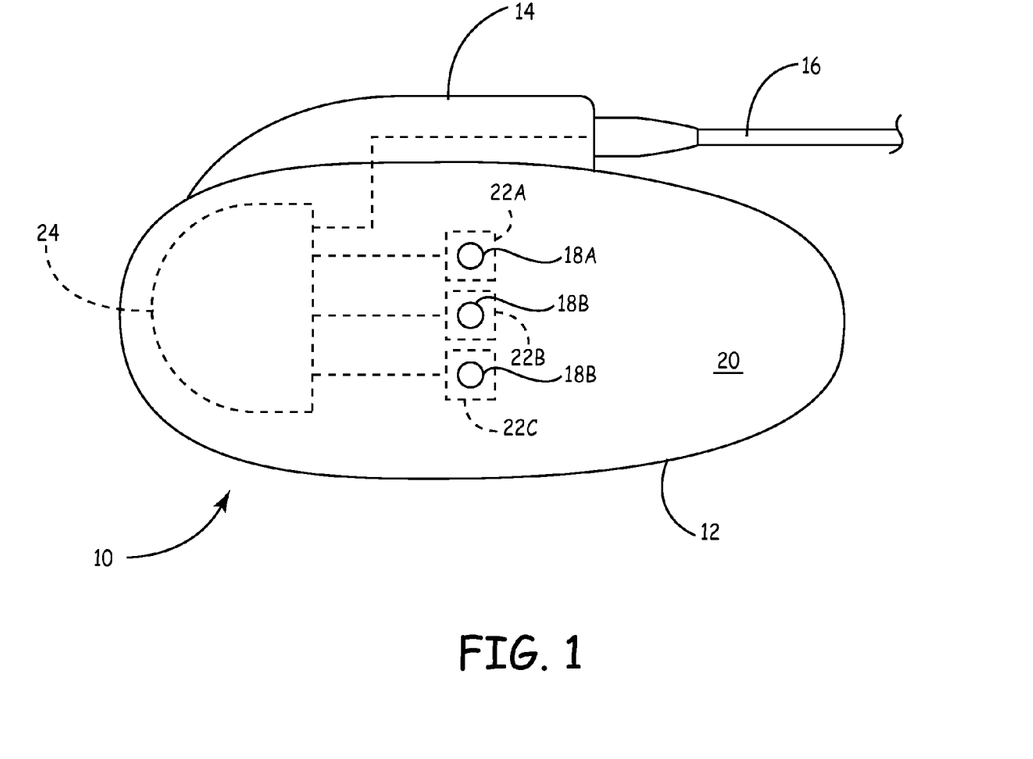
FIG. 1 is a front view of an ICD including miniaturized optical sensors.

FIG. 1 shows ICD 10, which includes housing or can 12, header 14, and one or more leads 16 for sensing electrical activity of the heart and delivering therapy in the form of pacing, cardioversion, or defibrillation. ICD 10 may include endocardial or epicardial leads that extend from the connector block assembly 14 to the heart. Alternatively, ICD 10 may be a subcutaneous (SubQ) or submuscular ICD that uses one or more electrodes on the exterior of can 12, together with a subcutaneous lead that carries a defibrillation coil electrode and a sensing electrode.

As shown in FIG. 1, can 12 includes three optical windows, 18A, 18B, and 18C in main surface 20 of can 12 (although a different number of optical windows can be used in other embodiments. Positioned behind optical windows 18A-18C are optical sensors 22A-22C respectively. Optical sensors 22A-22C are connected to main hybrid circuit 24, which includes circuitry for processing signals from lead 16, processing signals from optical sensors 22A-22C, and determining therapy to be delivered.

The use of three optical sensors 22A-22C allows selection of one the optical sensors to act as a light source, and one or both of the other two optical sensors to act as a light detector. Having multiple windows and multiple optical sensors allows optical reflectance sensing even if one of the windows is blocked with fatty tissue or bone, or if one of the windows is positioned near tissue that is not well perfused.

Each optical sensor 22A-22C includes multiple LEDs operating at different wavelengths. In the embodiment illustrated in FIGS. 2 and 3, each optical sensor includes three light emitting diodes (LED1, LED2, and LED3), each generating light of a different wavelength. In other embodiments, different numbers of light-emitting diodes may be used.

It is desirable to make optical sensors 22A-22C as small as possible. Each window 18A-18C introduces an opening in can 12 that is filled with a transparent window material different than the material forming can 12. Structural integrity is improved by making windows 18A-18C as small as possible. In addition, making optical sensors 22A-22C small is advantageous, since space within can 12 is limited, and there is a continuing effort to reduce the size of implantable medical devices.

Figure 2:
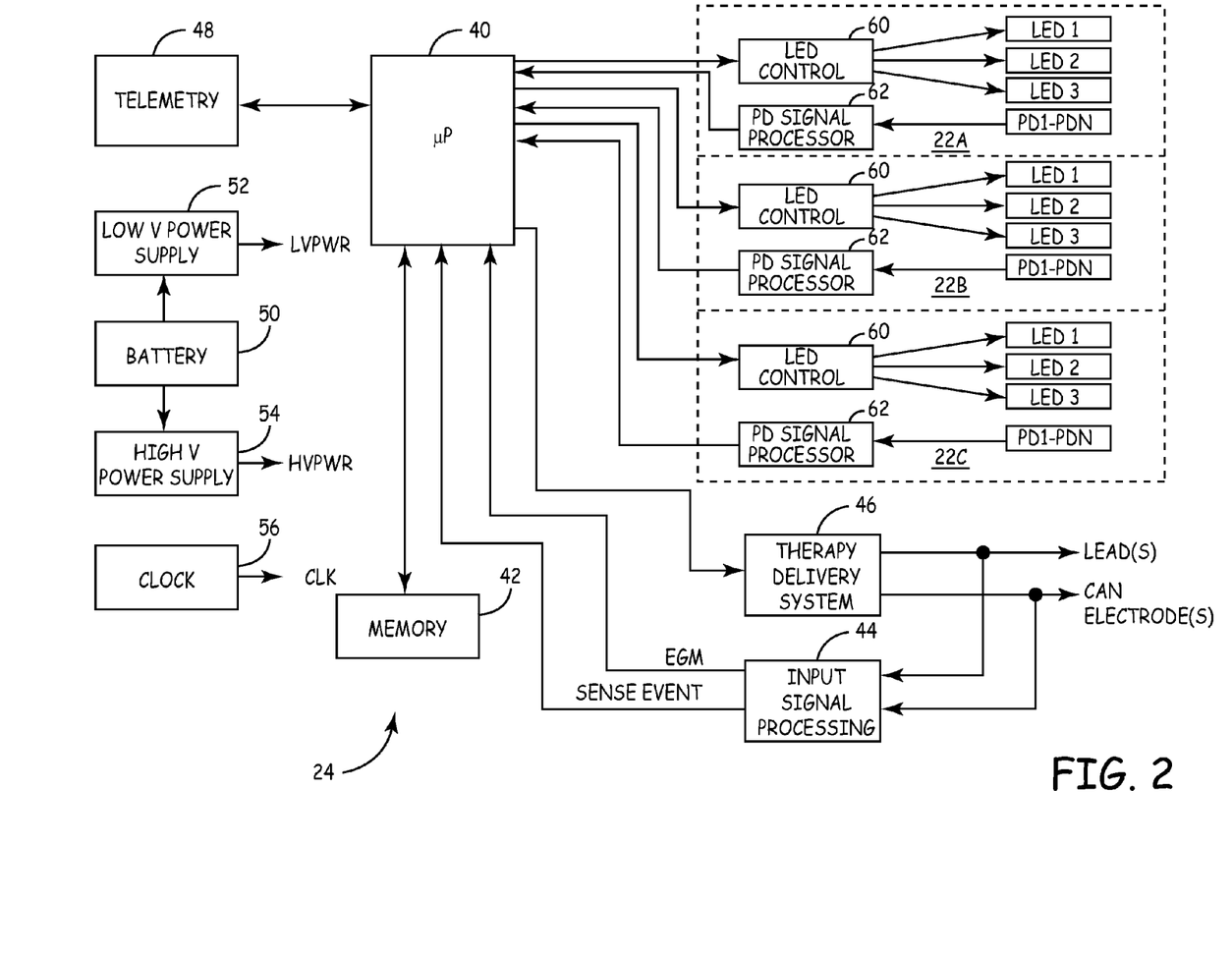
FIG. 2 is a block diagram of the ICD of FIG. 1.

FIG. 2 shows a functional block diagram of circuitry located within the interior of ICD 10. ICD 10 includes microprocessor 40, memory 42, input signal processing circuit 44, therapy delivery circuit 46, telemetry circuit 48, battery 50, low voltage power supply 52, high voltage power supply 54, and optical sensors 22A-22C. Each of optical sensors 22A-22C includes light-emitting diodes LED1-LED3, photodiodes PD1-PDN, LED control 60 and photodiode signal processor 62.

Microprocessor 40 controls the functions of ICD 10 by executing firmware program software algorithms stored in associated memory 42, such as ROM or RAM memory. Microprocessor 40 receives inputs from input signal processing circuit 44 and photodiode signal processor 62, and provides control signals to therapy delivery system 46 and LED control 60. Microprocessor 40 communicates with external devices through telemetry circuit 48.

Input signal processing circuit 44 receives signals from lead(s) 16 and from one or more electrodes on can 12. The outputs of input signal processing circuit 44 include digitized electrogram (EGM) waveforms and sense event signals derived from the electrodes on lead 16 and can 12.

Therapy delivery system 46 delivers cardiac pacing pulses to lead(s) 16 and can 12. Therapy delivery system 46 also includes circuitry for delivering cardioversion/defibrillation therapy in the form of electrical shocks, generally between lead(s) 16 and can 12.

Battery 50 supplies power to low voltage power supply 52 and high voltage power supply 54. Low voltage power supply 52 provides power to operate the circuitry of ICD 10, including power for pacing therapy. High voltage power supply 54 provides high voltage required by therapy delivery system 46 for high voltage cardioversion and defibrillation shocks. Clock circuit 56 provides clock signals used to control timing and to operate the circuitry of ICD 10.

Telemetry circuitry 48 allows microprocessor 40 to communicate with a remote or external device, such as a programmer (not shown). The communication may include commands from the programmer to configure the operation of ICD 10. In addition, microprocessor 40 can deliver data collected by ICD 10 to the programmer.

Optical sensors 22A-22C may be turned on by microprocessor 40 to gather additional data on which to make a determination whether a cardioversion/defibrillation shock is required. Microprocessor 40 uses various detection algorithms and criteria to analyze waveforms and sensed events from input signal processing circuit 44 in order to identify potential tachyarrhythmia or fibrillation. Optical sensors 22A-22C can provide additional data, as needed, for use by microprocessor 40 in determining the appropriate therapy.

Microprocessor 40 selects which optical sensor 22A-22C will function as the optical source, and which optical sensor (or sensors) will act as the detector. When activated by microprocessor 40, LED control 60 of one of optical sensors 22A-22C successively energizes LED1, LED2, and LED3. Each light-emitting diode LED1-LED3 emits a different wavelength. For example, LED1 emits infrared radiation at a wavelength of about 890 nm, LED2 emits near infrared radiation at a wavelength of about 810 nm, and LED3 emits red radiation at a wavelength of about 660 nm. In other embodiments, LEDs that emit radiation at other wavelengths may be used.

Photodiode signal processor(s) 62 of one (or both) of the other two optical sensors receives the photodiode signal from photodiodes PD1-PDN, which are connected in parallel. Photodiode signal processor 62 may include, for example, an integrator, an analog-to-digital (A/D) converter for converting the integrated photodiode signal to a digital signal, a transceiver, and a serial and/or parallel interface that sends data from optical sensor 22A-22C to microprocessor 40.

Figure 3:
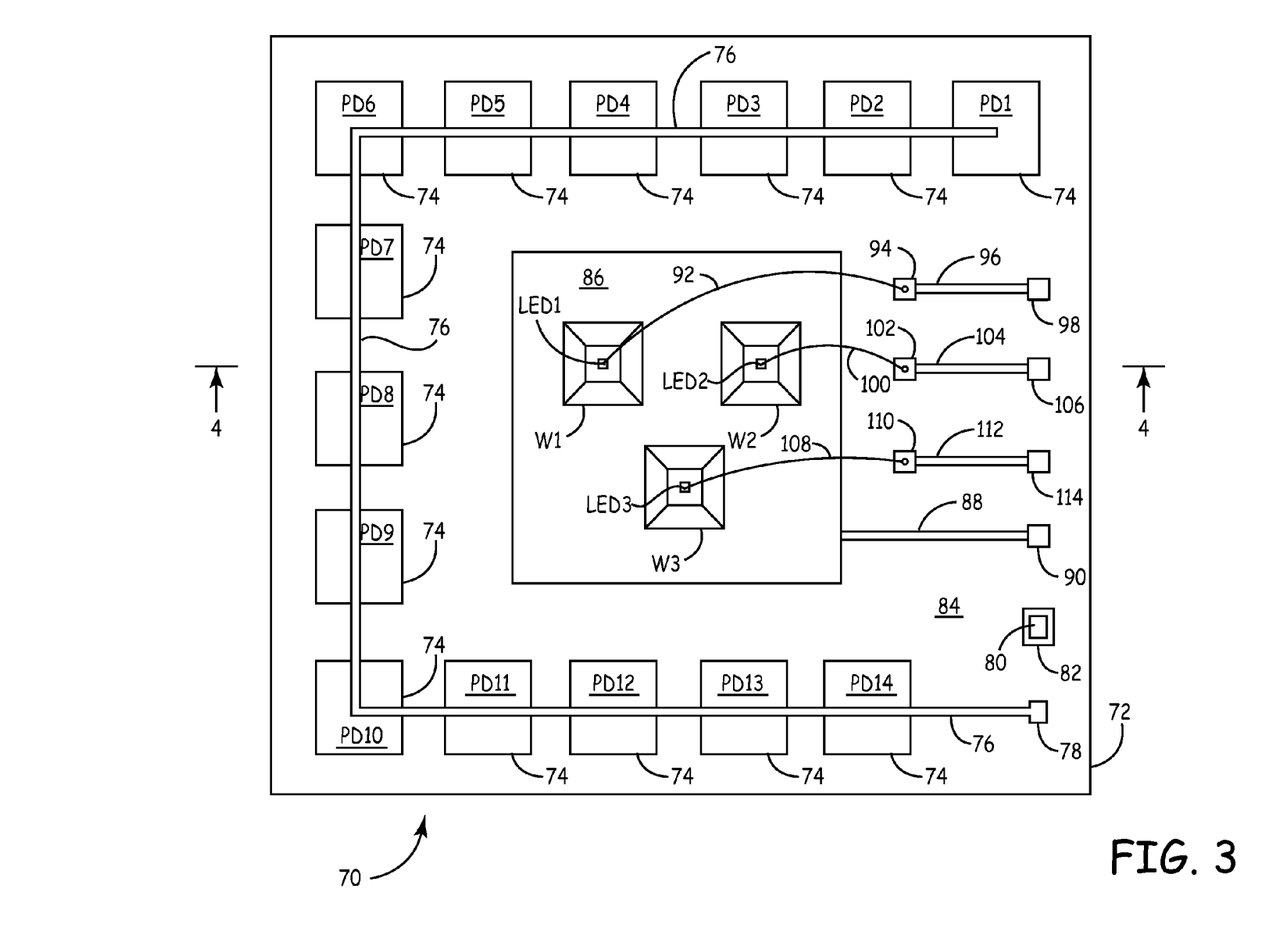
FIG. 3 is a top view of a miniaturized reflectance-type optical sensor.

FIG. 3 is a top view of integrated optical sensor 70, which includes photodiodes PD1-PD14 and light-emitting diodes LED1-LED3. Optical sensor 70 includes semiconductor substrate 72 which may be, for example, n-type silicon. Photodiodes PD1-PD14 are formed by p-type regions (anodes) 74 in n-type substrate 72, are connected in parallel. Photodiodes PD1-PD14 share a common cathode (n-type substrate 72), and p-type anodes 74 are all connected to electrical conductor 76, which is connected to contact pad 78. Substrate 72 is connected to contact pad 80, which extends through opening 82 in insulator layer 84 (for example, silicon dioxide) that covers the top surface of substrate 72. Photodiode signal processor 62 (shown in FIG. 2) is connected to contact pad 78 and 80 to receive a photodiode output that appears between contact pad 78 and 80.

Positioned in the center of optical sensor 70 are pyramidal wells W1-W3. Light-emitting diodes LED1-LED3 are mounted at the bottom of wells W1-W3, respectively. Metal layer 86 extends around and into wells W1-W3. Metal layer 86 forms a reflective layer on the sidewalls and bottom of wells W1-W3. Metal layer 86 functions, therefore, as both an optical mirror and as an electrical conductor to provide electrical connection to the anodes of light-emitting diodes LED1-LED3. Metal layer 86 is connected by metal trace 88 to contact pad 90. Examples of reflective metals that can be used for metal layer 86 include, for example, gold and silver.

The cathode of LED1 is connected by wire 92 to bond pad 94. Electrical trace 96 connects bond pad 94 to contact pad 98.

LED2 is connected by wire 100 to bond pad 102. Metal trace 104 connects bond pad 102 to contact pad 106.

LED3 has its cathode connected by wire 108 to bond pad 110. Electrical trace 112 connects bond pad 110 to contact pad 114.

Contact pads 90, 98, 106 and 114 are connected to LED control 60 shown in FIG. 2. LED1 is turned on by applying a current into contact pad 90 and out contact pad 98. Similarly, LED2 is turned on by applying a current into contact pad 90 and out contact pad 106. Light-emitting diode LED3 is turned on by applying a current into contact pad 90 and out contact pad 114.

Light-emitting diodes having a vertically arranged cathode and anode emit light both laterally and rearwardly from their sidewalls as well as from the top. As much as 40% of the total light emitted by a light emitting diode may be directed in a rearward direction toward a substrate. Wells W1-W3, together with metal layer 86, provide an optical mirror that redirects light emitted from light-emitting diodes LED1-LED3 in a direction which is generally perpendicular to the top surface of substrate 72. Wells W1-W3 can be formed by etching silicon substrate 72. The etching process creates sidewalls inclined at 54.7° (the 111 plane of silicon), and bottom 112 is flat (the 110 plane of silicon). Metal layer 86 can be formed with the same metal deposition that forms conductive traces 76, 88, 96, 104, and 112, bond pads 94, 102, and 110, and contact pads 78, 80, 90, 98, 106, and 114. For example, metal layer 86 may be silver or gold.

Other methods of forming wells in substrate 72 can also be used, such as standard photolithography techniques to define the region to be etched using photoresist, metal, oxide layers, etc. and then using a dry or wet etch to form the well. Well formation could use photolithography and ion implantation/diffusion to define the region of silicon to be etched. The dopant can be used to block etching (i.e. an etch stop on back side) or to enhance etching on the top side. Etching can also be used to create a circular or rectangular well with vertical, sloped, or curved (e.g. parabolic) walls.

Figure 4:
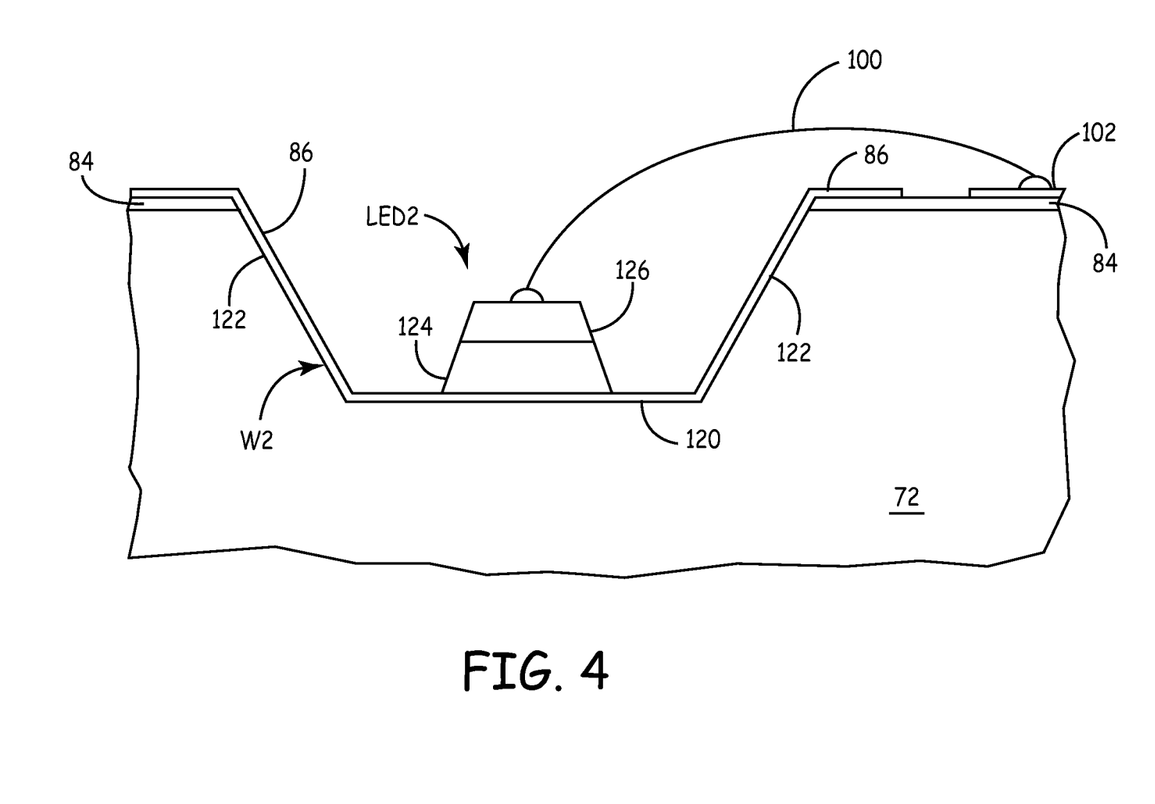
FIG. 4 is a sectional view along section 4-4 of FIG. 3.

FIG. 4 shows light-emitting diode LED2 mounted at bottom 120 of well W2. The top surface of LED2 is positioned within well W2 below top surface of substrate 72. As a result, light that is emitted generally laterally from LED2 will strike metal layer 86 on sidewalls 122 and be reflected upward out of well W2 in a direction that is generally perpendicular to the top surface of substrate 72. Light that is emitted rearwardly, such as due to Lambertian surface emission from side surfaces of LED2 may be redirected out of well W2 by reflection of metal layer 86 on the bottom of well W2, or by multiple reflections off metal layer 86 on the bottom and sidewalls.

As shown in FIG. 4, anode 124 of LED2 is in electrical contact with metal layer 86 on bottom 120. Cathode 126 is positioned above anode 124, and is connected to bond pad 102 by wire 100. In other embodiments, anode 124 and cathode 126 may be inverted from the configuration shown in FIG. 4.

Figure 5:
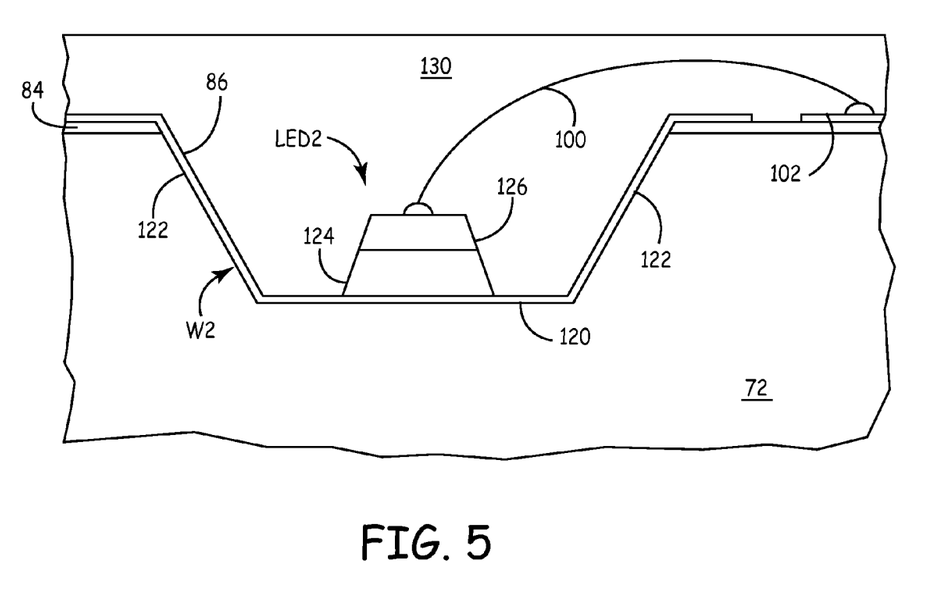
FIG. 5 shows a sectional view of a further embodiment of the optical sensor with a polymeric lens formed over the light-emitting diode.

Although optical sensor 70 uses an array of photodiodes connected parallel to form the photodetector, the number of photodiodes may vary, and a single large photodiode extending around wells W1-W3 could also be formed. The use of multiple smaller photodiodes PD1-PD14 in connected in parallel, rather than a single larger photodiode, reduces the effective capacitance associated with the photodiodes, but can also reduce light collection efficiency. Both photodiodes PD1-PD14 and light-emitting diodes LED1-LED3 could also have a lens or index matching optical element deposited over them. The lens or index-matching layer can be formed, for example, by a spin on polymer coating applied after light-emitting diodes LED1-LED3 are mounted in wells W1-W3, respectively. FIG. 5 shows an example of a layer 130 deposited over LED2. The polymer coating fills well W2, and extends above the top surface of substrate 72. In some embodiments, the spin on polymer layer may also be used as a dielectric or insulating layer to electrically isolate the components of optical sensor 70 from can 12. This can be advantageous in those instances where can 12 is being used as an electrode in the application of high voltage cardioversion/defibrillation shocks.

In FIG. 5, the top surface of lens or index matching layer 130 is shown as being planar. In other embodiments, the top surface may be non-planar, such as a convex shape for focusing more of the emitted light into the direction generally perpendicular to the top surface of substrate 72. Individual convex lens shapes can be formed over wells W1-W3, so that each light emitting diode LED1-LED3 has its own convex lens.

Although integrated sensor 70 is shown as including only photodiodes PD1-PD14 and light-emitting diodes LED1-LED3, in other embodiments additional components may be formed in substrate 72. For example, LED control circuitry 60 and photodiode signal processor circuitry 62 may also be formed in substrate 72. Although substrate 72 has been described in one example as being n-type material, in other embodiments it may be p-type material. In other embodiments, the photodiodes may be formed as separate elements, and then attached to substrate 72.

In some embodiments, multiple light-emitting diodes may be positioned within a single well. In those cases, however, the light-emitting diodes will provide some shadowing of one another, so that the amount of light emitted will be reduced.

Figure 6:
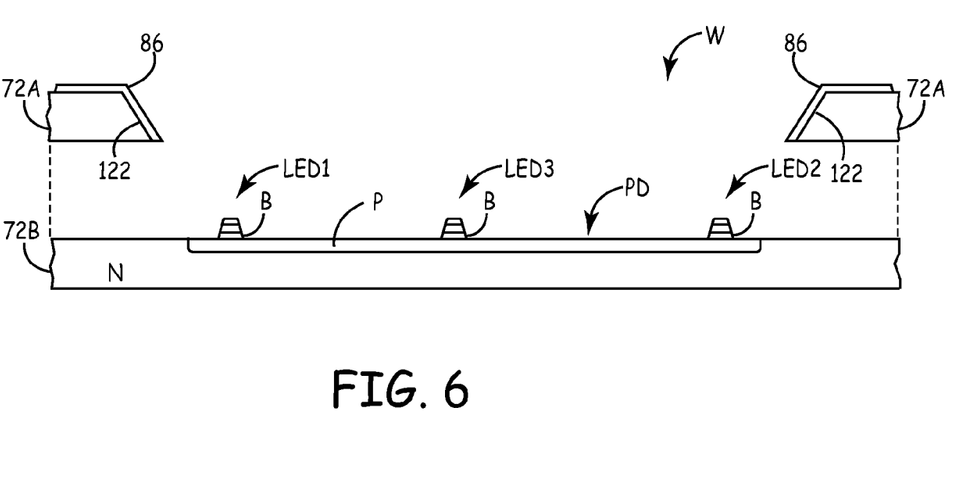
FIG. 6 shows an exploded view of an embodiment of an optical sensor with a two part substrate with a photodiode and LEDs positioned in a common well.

FIG. 6 shows an exploded view of another embodiment, in which substrate 72 is formed by upper portion 72A and lower portion 72B. In this embodiment, upper portion has been etched through to define the inclined sidewalls 122, and metal layer 86 is deposited sidewalls 122 and the top surface of upper portion 72A. Upper portion 72A is placed over lower portion 72B, and the portions are bonded together.

In FIG. 6, photodiode PD is formed in lower portion 72B, and is positioned at the bottom of well W with LED1-LED3. In FIG. 6, LED1, LED2, and LED3 are mounted on bond pads B on the upper surface of photodiode PD. Electrical connections for both photodiode PD and light-emitting diodes LED1-LED3 can be provided, for example, by wires similar to wires 92, 100, and 108 shown in FIG. 3. Alternatively, electrical conductors can be formed on the top surface of lower substrate portion 72B to connect to LED1-LED3 and photodiode PD, and connections can be made to those conductors through holes formed in upper substrate portion 72A. The assembly and bonding of substrate portions 72A and 72B may occur either before or after light-emitting diodes LED1-LED3 are mounted above photodiode PD.

Figure 7:
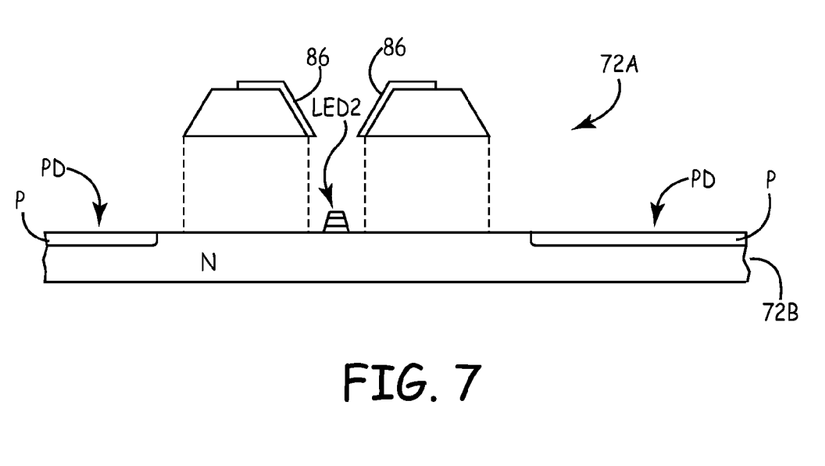
FIG. 7 shows an exploded view of another embodiment of an optical sensor with a two part substrate.

FIG. 7 shows another embodiment using a two part substrate. In this embodiment, photodiode PD is again formed in lower portion 72B. Upper portion 72A defines a well for each LED (in FIG. 7, only LED2 is shown), and is also etched or cut so that it does not cover photodiode PD. Like FIG. 6, both photodetectors (e.g. photodiode PD) and light-emitting diodes (e.g. LED2) are mounted on lower portion 72B of substrate 72, but in this case they do not share the well in which LED2 is located.

The optical mirror on the sidewalls of a well can also be used in other optical devices that include an LED. A photodetector may not be required in some optical devices, and other types of components may be fabricated in or mounted on the substrate.

In summary, an optical device, such as an integrated optical sensor which includes both the photodetector (such as photodiodes) and a light source (light-emitting diodes mounted within reflectively-coated wells of the substrate), offers minimized power, minimized size, maximized signal-to-noise ratio for optical measurement, and operational redundancy and flexibility. The optical reflectance measurement provided by the sensor can be used in a variety of different applications. It is particularly advantageous for the use of medical devices to provide oxygen or tissue perfusion measurements.

Although the present invention has been described with reference to preferred embodiments, workers skilled in the art will recognize that changes may be made in form and detail without departing from the spirit and scope of the invention.

The invention claimed is:

1. An optical device for an implantable medical device comprising:
   a substrate;
   a well in the substrate having sidewalls and a bottom surface;
   a reflective coating on at least one of the bottom surface and the sidewalls of the well;
   a light emitting diode mounted on the flat bottom surface of the well; and
   a photodetector in the substrate and configured for receiving light emitted by the light emitting diode, wherein the substrate comprises an upper substrate portion bonded to a lower substrate portion, the photodetector being in the lower substrate portion.

2. The device of claim 1, wherein the reflective coating comprises an electrically conductive material.

3. The device of claim 2, wherein the reflective coating is connected to a first contact pad.

4. The device of claim 3, wherein the light emitting diode includes a lower electrode connected to the reflective coating.

5. The device of claim 4, wherein the light emitting diode includes an upper electrode electrically connected to a second contact pad.

6. The device of claim 1, wherein the light emitting diode is mounted in the well so that an upper surface of the light emitting diode is located below an upper end of the well.

7. The device of claim 1, wherein the substrate comprises a semiconductor material.

8. The device of claim 1, wherein the substrate includes a first conductivity type region, and wherein the photodetector includes at least one photodiode formed by a region of a second conductivity type in the substrate.

9. The device of claim 8, wherein the photodetector comprises a plurality of photodiodes connected in parallel.

10. The device of claim 7, wherein the semiconductor material comprises silicon.

11. The device of claim 10, wherein the sidewalls of the well are inclined at about 54.7°.

12. The device of claim 1 and further comprising:
a polymeric material over at least a portion of the substrate.

13. The device of claim 11, wherein the polymeric material fills the well to form an optical element over the light emitting diode.

14. The device of claim 1, wherein the sidewalls of the well are inclined.

15. The device of claim 14, wherein the well has a pyramidal shape.

16. The device of claim 1 and further comprising:
a photodetector positioned adjacent the well.

17. The device of claim 1 and further comprising:
a photodetector positioned at the bottom of the well.

18. The device of claim 1, wherein the upper substrate portion defines the well sidewalls, and the lower substrate portion defines the well bottom surface.

19. An optical sensing device for an implantable medical device comprising:
a substrate having a generally planar top surface;
a plurality of wells extending into the substrate from the top surface, each well having inclined sidewalls and a bottom surface;
a plurality of light emitting diodes, each of the light emitting diodes mounted on the bottom surface of a different one of the wells;
a reflective metal coating on at least one of the bottom surface and the sidewalls of the wells; and
a photodetector in the substrate adjacent the plurality of wells,
wherein the substrate comprises an upper substrate portion bonded to a lower substrate portion, the photodetector being in the lower substrate portion.

20. The device of claim 19, wherein the photodetector comprises a plurality of photodiodes.

21. The device of claim 20, wherein the photodiodes are connected in parallel.

22. The device of claim 20, wherein the photodiodes are formed in the substrate.

23. The device of claim 20 and further comprising contact pads for providing electrical connection to the light emitting diodes and the photodiodes.

24. The device of claim 19, wherein each of the light emitting diodes emits light at a different primary wavelength.

25. The device of claim 19, wherein the reflective metal coating provides an electrical connection to one electrode of each of the light emitting diodes.

26. The device of claim 19, wherein the substrate comprises a semiconductor material.

27. The device of claim 19, wherein an upper surface of each of the light emitting diodes is positioned below the top surface of the substrate.

28. The device of claim 27 and further comprising:
a polymeric material filling the wells.

29. The device of claim 19, wherein each of the wells includes four inclined sidewalls.

30. An implantable medical device comprising:
a housing having a wall with a plurality of windows;
a plurality of optical reflectometers, each reflectometer positioned adjacent to one of the windows and comprising:
a substrate having a generally planar top surface;
a plurality of wells extending into the substrate from the top surface, each well having inclined sidewalls and a bottom surface;
a plurality of light emitting diodes, each of the light emitting diodes mounted on the bottom surface of a different one of the wells;
a reflective metal coating on at least one of the bottom surface and the sidewalls of the wells; and
a photodetector in the substrate adjacent the plurality of wells,
wherein the substrate comprises an upper substrate portion bonded to a lower substrate portion, the photodetector being in the lower substrate portion.

31. The device of claim 30, wherein each of the light emitting diodes emits light at a different primary wavelength.

32. The device of claim 31, wherein each reflectometer includes three light emitting diodes that emit light at an infrared primary wavelength, a near infrared primary wavelength, and a red primary wavelength, respectively.

33. The device of claim 30 and further comprising:
a processor for controlling which of the reflectometers acts as a light source and which of the reflectometers acts as a light detector.

34. The device of claim 33 and further comprising:
a therapy delivery system controlled by the processor.

35. The device of claim 34, wherein the processor controls therapy delivered by the therapy delivery system based at least in part by signals received from the reflectometers.

36. The device of claim 30, wherein the photodetector comprises a plurality of photodiodes.

37. The device of claim 30, wherein the reflective metal coating includes a region on the top surface surrounding the wells.

38. The device of claim 30, wherein the reflective metal coating provides an electrical connection to one electrode of each of the light emitting diodes.

39. The device of claim 30, wherein the substrate comprises a semiconductor material.

40. device of claim 30, wherein an upper surface of each of the light emitting diodes is positioned below the top surface of the substrate.

41. The device of claim 40 and further comprising:
a polymeric material filling the wells.

42. The device of claim 30 and further comprising contact pads for providing electrical connection to the light emitting diodes and the photodetector.

\* \* \* \* \*